United States Patent
Stanley et al.

(10) Patent No.: US 11,064,889 B2
(45) Date of Patent: Jul. 20, 2021

(54) METHOD OF EVALUATING AND VISUALIZING FIT OF AN APPLICATOR

(71) Applicant: The Procter & Gamble Company, Cincinnati, OH (US)

(72) Inventors: Scott Kendyl Stanley, Mason, OH (US); Andrew Paul Rapach, Fairfield, OH (US); Robert Webbink, Sharonville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/528,693

(22) Filed: Aug. 1, 2019

(65) Prior Publication Data

US 2020/0046226 A1 Feb. 13, 2020

Related U.S. Application Data

(60) Provisional application No. 62/715,300, filed on Aug. 7, 2018.

(51) Int. Cl.

| | | |
|---|---|---|
| *A61B 5/00* | (2006.01) | |
| *G06T 7/50* | (2017.01) | |
| *G06T 7/30* | (2017.01) | |
| *G06F 30/20* | (2020.01) | |
| *G06T 7/00* | (2017.01) | |
| *G06T 19/20* | (2011.01) | |

(52) U.S. Cl.
CPC ............ *A61B 5/0064* (2013.01); *G06F 30/20* (2020.01); *G06T 7/0014* (2013.01); *G06T 7/30* (2017.01); *G06T 7/50* (2017.01); *G06T 19/20* (2013.01); *G06T 2207/30088* (2013.01); *G06T 2207/30201* (2013.01); *G06T 2219/2004* (2013.01)

(58) Field of Classification Search
CPC .......... A61B 5/0064; G06T 7/50; G06T 7/30; G06T 7/0014; G06T 19/20; G06F 30/20
USPC ....................................................... 345/589
See application file for complete search history.

(56) References Cited

U.S. PATENT DOCUMENTS

| | | | |
|---|---|---|---|
| 2006/0023228 A1* | 2/2006 | Geng ..................... | A61B 5/411 356/601 |
| 2008/0060652 A1* | 3/2008 | Selvarajan ........ | A61M 16/0666 128/206.21 |
| 2012/0192884 A1* | 8/2012 | Nasu ........................ | A45F 3/18 132/200 |

(Continued)

FOREIGN PATENT DOCUMENTS

| | | |
|---|---|---|
| JP | 2010131091 A | 6/2010 |
| WO | WO2012137942 A1 | 10/2012 |

OTHER PUBLICATIONS

International Search Report and Written Opinion, U.S. Appl. No. 16/528,693, dated Oct. 17, 2019, 14 pgs.

*Primary Examiner* — Hai Tao Sun
(74) *Attorney, Agent, or Firm* — Sarah M DeCristofaro (57) ABSTRACT

A method for evaluating fit of an applicator can include receiving on a process first and second sets of digital data representing the target area and at least a portion of the applicator, respectively, digitally overlying the second set of digital data over the first set of digital data; calculating in the target area at a plurality of points of the overlay a separation distance between the sets of data and generating an electronic image that includes a visual depiction of the calculated separation distance.

30 Claims, 7 Drawing Sheets

(56) References Cited

U.S. PATENT DOCUMENTS

| | | | |
|---|---|---|---|
| 2014/0278319 A1* | 9/2014 | Thiruvengada | A62B 7/04 703/11 |
| 2017/0008566 A1 | 1/2017 | Willerton | |
| 2017/0354805 A1 | 12/2017 | Stanley et al. | |
| 2017/0354806 A1 | 12/2017 | Stanley et al. | |
| 2018/0028772 A1* | 2/2018 | Davis | A61B 5/4818 |

* cited by examiner

METHOD OF EVALUATING AND VISUALIZING FIT OF AN APPLICATOR

FIELD OF THE DISCLOSURE

The disclosure relates to methods for evaluating and/or visualizing and/or comparing fit or effective coverage area of an applicator when applied to a target area.

BACKGROUND OF THE DISCLOSURE

Agents for affecting target structures are well known. Temperature affects may be induced by the application of hot or cold agents to the target. The appearance of a target may be affected by cosmetic and decorative agents. Electric current, voltages, and electric and magnetic fields may be applied to a target using local applicators. For biological targets, surface properties may be impacted by the use of topical application of moisturizers, medicaments and other treatment actives.

The effectiveness of the active agent may be impacted by the nature of the applicator available to facilitate the interaction of the active agent with the target structure. Typical applicators are less than precise with respect to their conformance to the target structure and the use of one-size, or a few sizes, fits all tends to compromise the actual performance of the active agent. In particular, conventional one-size fits all applicators for facial products, for example, typically have universally large eye and lip openings to accommodate variations in user's features. As a result, such applicators are ineffective at applying an active agent in the region of the eye or the lips in many individuals. Additionally, such applicators can result in gapping or bubbling in certain areas, such as around the nose region. Thus, despite appearing to fit from an external view, the gaps and bubbles result in ineffective application of the treatment to the target surface.

SUMMARY OF THE DISCLOSURE

In accordance with embodiments, a method for evaluating a fit of an applicator on a target area can include receiving on a processor a first set of digital data representing the target area, the first set of data being received from a digital geometric representation of the target area streamed in real time or stored on a memory; and receiving on the processor a second set of digital data representing at least a portion of an applicator designed to contact the target area. The method can further include digitally overlying the second set of digital data over the first set of digital data to determine digitally the contact area of the at least the portion of the applicator when applied to the target area; and calculating in the target area at a plurality of points of the overlay a separation distance between the second set of digital data and the first set of digital data, wherein a separation distance of about 1 mm or less represents contact between the applicator and the target area when the applicator is applied to the target area. The method can also include generating a first electronic image that includes a visual depiction of the calculated separation distance between the applicator and the target area when the applicator is applied to the target area. The method can further include generating a second image that includes a visual depiction of the calculated separation distance between a second applicator and the target area when the second applicator is applied to the target area.

In accordance with embodiments, a method for comparing a fit of a first applicator to a second applicator when applied to a target area can include receiving on a processor a first set of digital data representing the target area, the first set of data being received from a digital geometric representation of the target area stored on a memory; receiving on the processor a second set of digital data representing at least a portion of a first applicator designed to contact the target area, wherein the first applicator is a one-size fits all applicator; and receiving on the processor a third set of digital data representing at least a portion of a second applicator designed to contact the target area, wherein the second applicator is created from a digital geometric representation of the target area, or is created from measurements of the target area of a particular individual. The method can further include digitally overlying the second set of digital data over the first set of digital data to determine digitally the contact area of the at least the portion of the first applicator when applied to the target area; digitally overlying the third set of digital data over the first set of digital data to determine digitally the contact area of the at least the portion of the second applicator when applied to the target area. The method can also include calculating in the target area at a plurality of points of the overlay a separation distance between the second set of digital data and the first set of digital data, wherein a separation distance of about 1 mm or less represents contact between the first applicator and the target area when the first applicator is applied to the target area; and calculating in the target area at a plurality of points of the overlay a separation distance between the third set of digital data and the first set of digital data, wherein a separation distance of about 1 mm or less represents contact between the second applicator and the target area when the second applicator is applied to the target area. The method further can include generating a first electronic image that includes a visual depiction of the calculated separation distance between the first applicator and the target area when the applicator is applied to the target area; and generating a second electronic image that includes a visual depiction of the calculated separation distance between the second applicator and the target area when the applicator is applied to the target area. In various embodiments, the first and second electronic images provide visual comparisons of the effectiveness of coverage of the first and second applicators, and can illustrate improved coverage, fit, and/or performance achieved by the second applicator.

In any of the embodiments herein, the target area can be the human face or a portion thereof. In any of the embodiments herein, the applicator can be a mask for applying an active, therapeutic, and/or cosmetic agent to the human face or portion thereof. In any embodiments herein, the target area can be another part of the body, such as a hand or foot, and the applicator can be a treatment article, brace, support, or orthotic. In any of the embodiments herein, the target area may be a foot or portion of a foot or feet. Alternately, in any embodiment, the fit visualization may pertain to the fit of an orthotic into an existing shoe (to show both the fit of the orthotic to the foot and then separately or together, show the fit of the orthotic to a particular shoe). By orthotics we mean to include, without limitation: supports, masks, insoles, inserts, correctives, levelers, shock absorbers, odor control, and any other prothesis devices intended for use on treating gait, blisters, bunions, fungus, infections, toenail problems, muscular or skeletal support issues, joint issues, or any other health issues or sports performance issues or improving general comfort and or mobility.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Applicators can appear to have a "good" or comfortable fit from an external perspective, but be ineffective if the area contacted or occluded by the applicator is not sufficient and/or there are gaps or bubbles in target areas. When there is insufficient contact or gapping or bubbling, active, therapeutic, and/or cosmetic agents provided on the applicator cannot reach the skin and/or cannot be provide in a sufficient dosage where there is insufficient contact. Additionally, one-size-fits-all applicators are too big for some and too small for others, and cannot accommodate a variety of face shapes. Methods in accordance with embodiments of the disclosure can allow for visualization of the internal fit of the applicator, illustrating the occluded regions of the target area by the applicator and allowing for improved evaluation of applicator fit and/or effectiveness.

As used herein and unless otherwise specified, the "fit" of the applicator refers to an effectiveness of the applicator in contacting the target areas. An applicator having good fit or effectiveness of contact can include an applicator having at least about 90%, at least about 92%, at least about 95%, at least about 97%, at least about 99% or 100% contact of the intended target area. For example, an applicator having a good fit and effective contact of a target area can cover about 90, 91, 92, 93, 94, 95, 96, 97, 98, 99, or 100% of the target areas and any range of contact percentage therein.

In embodiments, the intended target area can be, for example, the entire face of a user or a portion of the face. In such embodiments, the applicator can be a mask for covering the face or a portion or portions thereof. For example, the intended target area can be an eye area. Conventional masks can suffer from ineffective coverage of the eye area, particularly the under-eye area as a result of eye openings that are too large or bubbles or gapping that forms in the under-eye region and typically between the edge of the nose and the under-eye area. In another or further embodiment, the target area can be the corner of the nose, outside the nostrils. Conventional mask can suffer from gapping at this region, resulting in limited or no contact of this region. Any specific region or regions of the face can be used as the target area or the entire face can be the target area.

Figure 1:
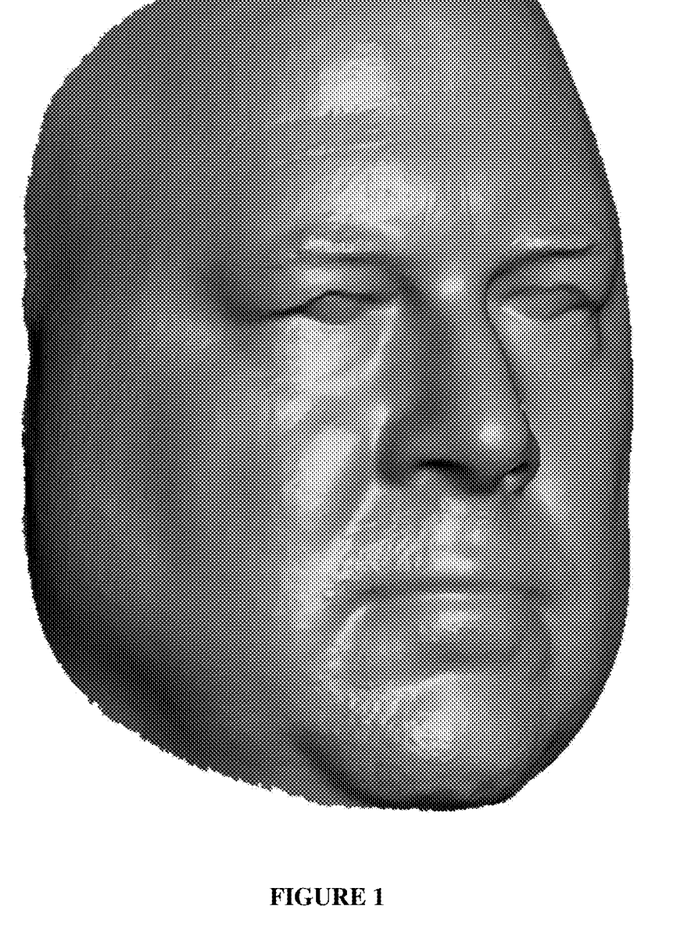
FIG. 1 is a digital geometric representation of a face for use in methods in accordance with embodiments of the disclosure.
Figure 3:
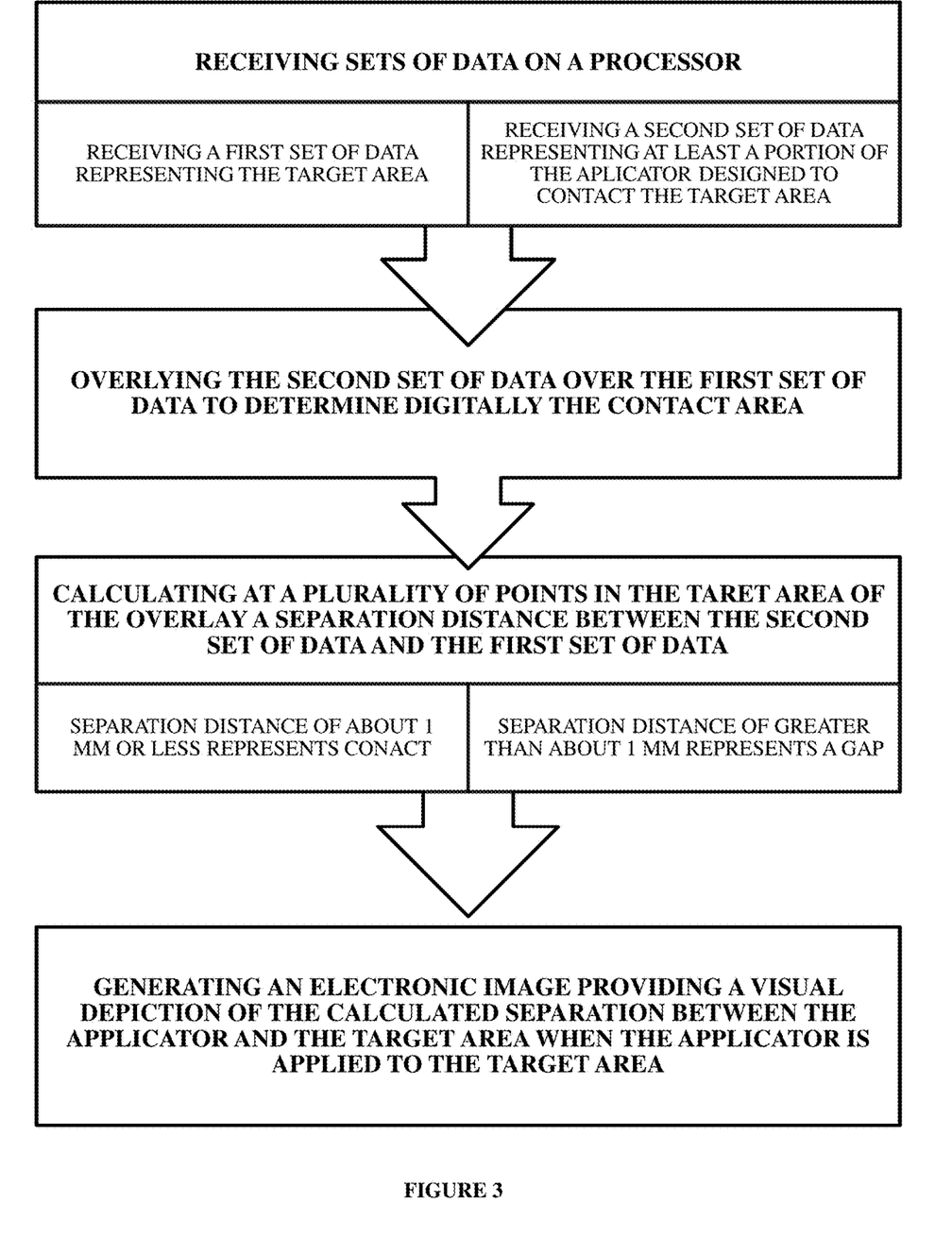
FIG. 3 is a process diagram illustrating a method in accordance with other embodiments of the disclosure.
Figure 4:
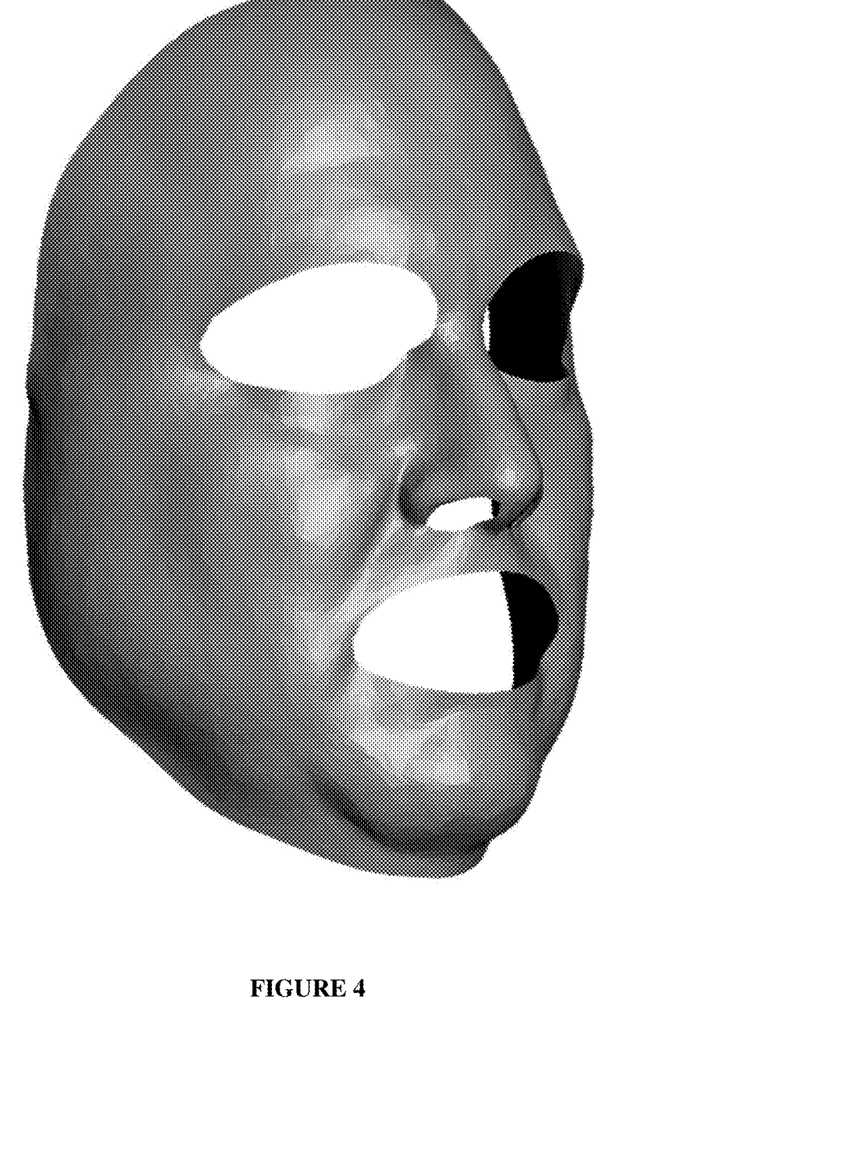
FIG. 4 is a digital geometric representation of a mask for use in methods in accordance with embodiments of the disclosure.
Figure 5:
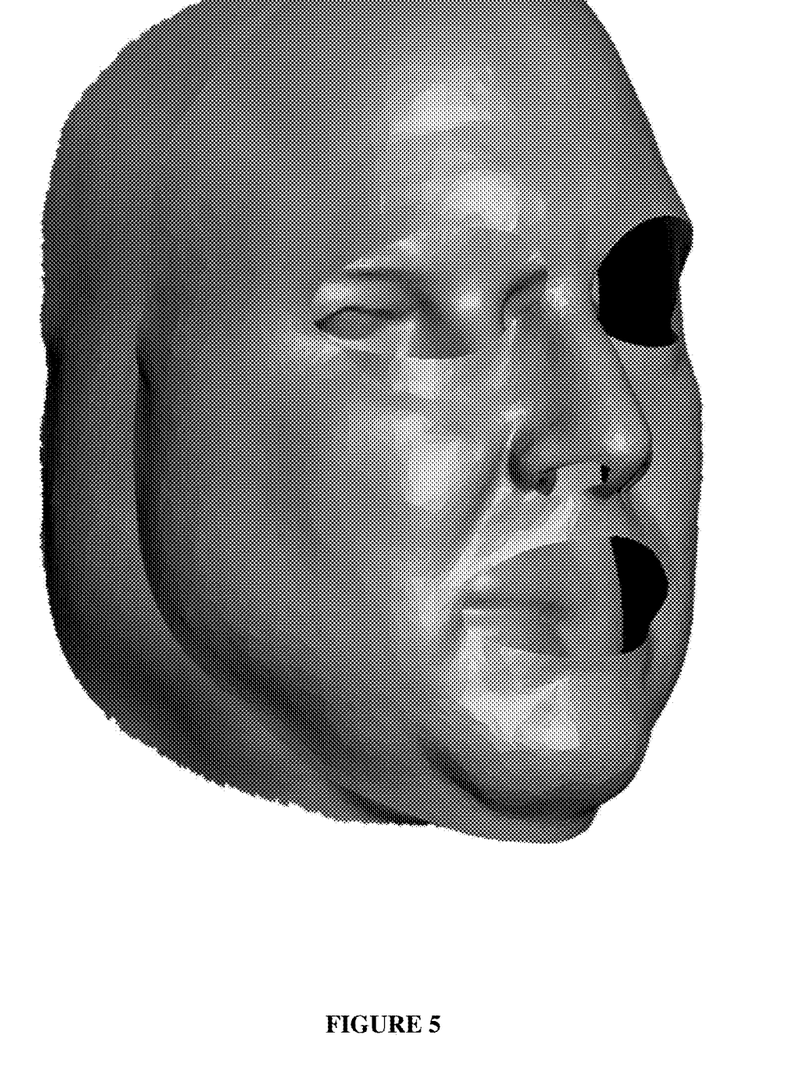
FIG. 5 is a graphical illustration of digitally overlaying data associated with the digital geometric representation of the mask of FIG. 4 over data associated with the digital geometric representation of the face of FIG. 1.
Figure 6:
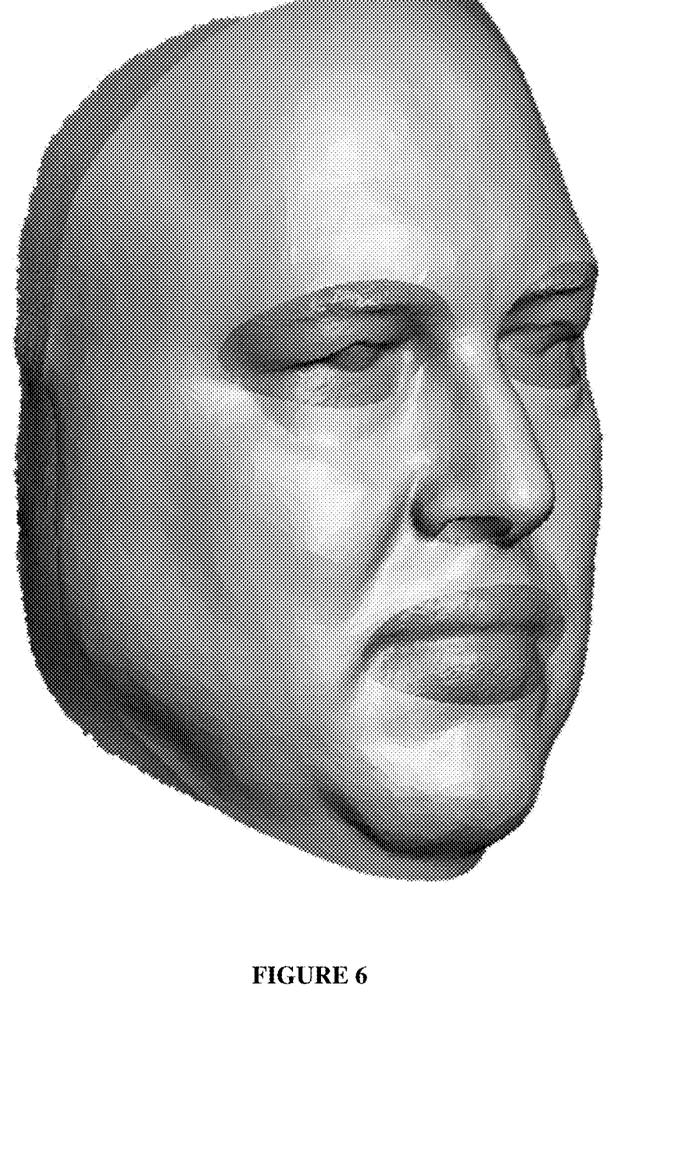
FIG. 6 is a graphical illustration of the result of the digital overlay of FIG. 5.
Figure 7:
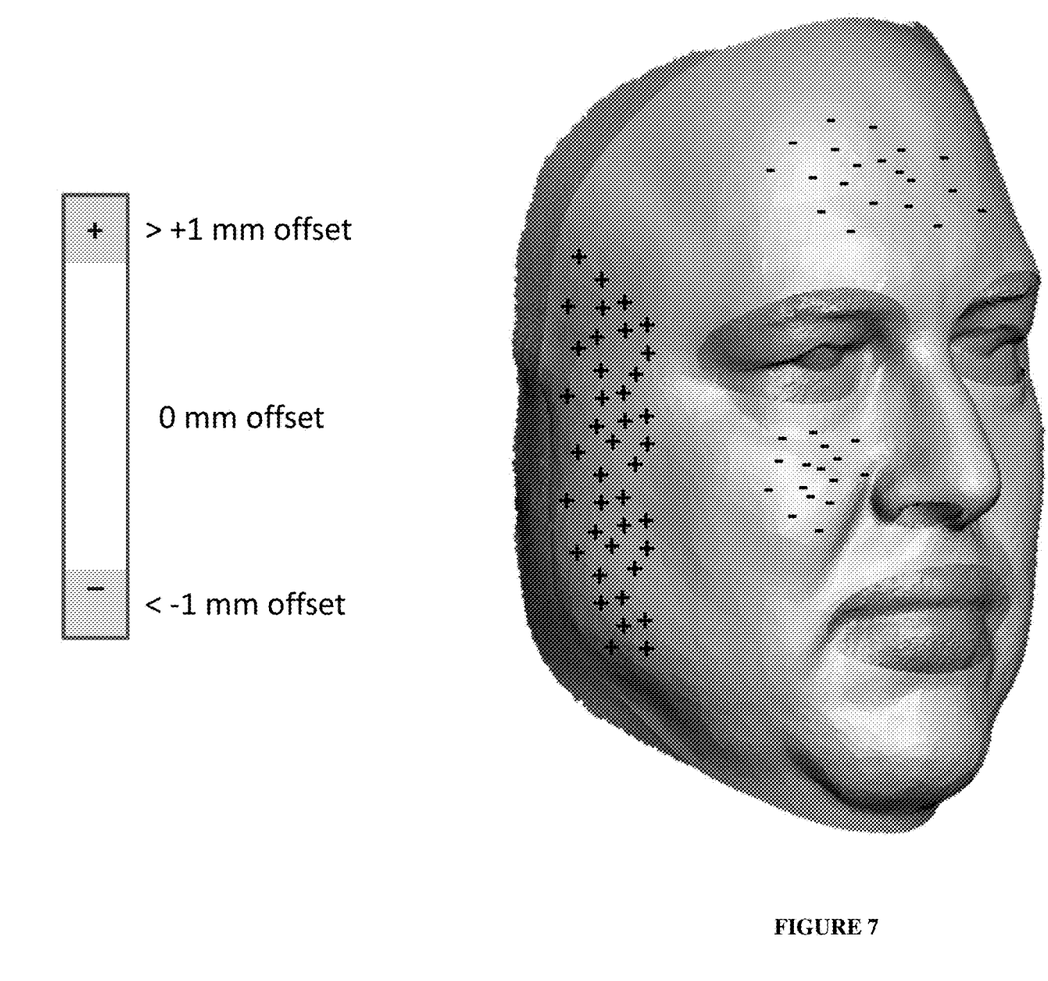
FIG. 7 is a difference map illustrating a separation distance at a plurality of points of the mask of FIG. 4 to the face of FIG. 1 in accordance with methods of the disclosure.

Referring to FIG. 3, in accordance with embodiments, a method of determining fit of an applicator on a target area can include receiving on a processor a first set of digital data representing the target area. The first set of digital data can be received from and/or generated from a geometric representation of the target area. FIG. 1 illustrates a digital geometric representation of a face as the target area. The method can further include receiving on the processor a second set of digital data representing at least a portion of an applicator or mask designed to cover the target area when applied. FIG. 4 illustrates a digital graphical representation of the second set of data for a face mask. As illustrated in FIGS. 5 and 6, the second set of digital data can then be overlaid over the first set of digital data to determine digitally the contact area of the applicator when it is applied to the target area. The method can further include calculating at a plurality of points of the overlay a separation distance between the second set of data and the first set of data. A separation distance of about 1 mm or less can represent contact between the applicator and the target area when it is applied. At greater separation distances, a gap may occur between the applicator and the target area, which can make application of the active, therapeutic, and/or cosmetic agent disposed on the applicator less effective. The method can further include generating a first electronic image that includes a visual depiction of the calculated separation distance between the applicator and the target area. FIG. 7 illustrates a graphical representation of a difference map illustrating the separation distance between the first and second sets of data for a face mask and corresponding face structure. While FIG. 7 illustrates the difference by way of symbols (+ and −), other methods of illustrating a difference can be used, such as color mapping and heat mapping. Such illustrations of the separation can be displayed on any suitable display including, but not limited to, television displays, monitors, mobile phone applications, and virtual reality systems.

Figure 2:
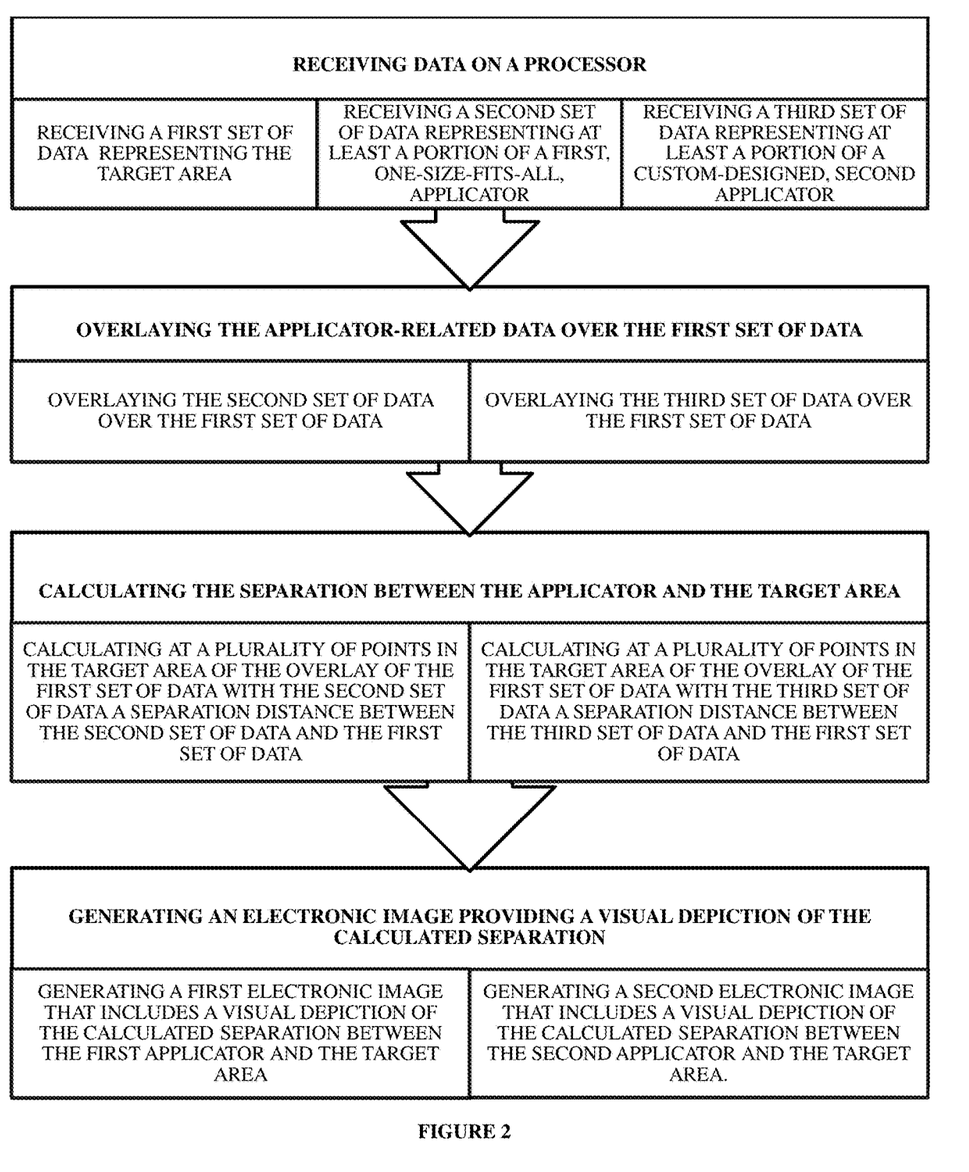
FIG. 2 is a process diagram illustrating a method in accordance with other embodiments of the disclosure.

Referring to FIG. 2, in embodiments of the method, a method of comparing fit of a first applicator to a second applicator can include receiving on a processor a first set of data representing the target area, receiving on a processor a second set of data representing at least a portion of a first applicator designed to cover the target area, and receiving on a process a third set of data representing a second applicator designed to cover the target area. The data can be received on the same processor in embodiments or can be received on multiple processors. The method can further include digitally overlaying the second set of data over the first set of data and calculating at a plurality of points of the overlay a separation distance between the second set of data and the first set of data. The method also includes digitally overlaying the third set of data over the first set of data and calculating at a plurality of points of the overlay a separation distance between the third set of data and the first set of data. The method can also include generating a first electronic image that includes a visual depiction of the calculated separation distance between the second set of data and the first set of data, thereby illustrating the coverage of the first applicator on the target area. The method can also further include generating a second electronic image that includes a visual depiction of the calculated separation distance between the third set of data and the first set of data, thereby illustrating the coverage of the second applicator on the target area. The first and second images can be used to compare the coverage area or fit of the first and second applicators. The methods steps for receiving, overlying, and calculating the separation distances for the second set of data and the third set of data can be performed in parallel or can be performed sequentially in any desired ordered. FIG. 2 illustrates a process diagram showing performance of the method steps for the second and third sets of data running in parallel by way of example only. For example, the method can be performed such that the separation distance between the third set of data and the first set of data is calculated before the separation distance between the second set of data and the first set of data is calculated. Any suitable order can be used.

In embodiments, the method can include generating a visual depiction comparing the first electronic image to the second electronic image. For example, the visual depiction can be a side-by-side view of the first and second electronic images. In embodiments, the method can include displaying the first electronic image before the second electronic image. In embodiments, the method can include displaying the second electronic image before the first electronic image.

In embodiments, the method can further include overlying the first and second electronic images to generate a third electronic image illustrating the comparison of coverage area between the first and second applicators. In embodiments, the method can include generating a third electronic image that includes a visual depiction of regions in which at least 90% of the plurality of points have a separation distance of 1 mm or less only in the overlay of the third set of data with the first set of data, but not in the overlay of the second set of data with the first set of data, thereby visually depicting improved coverage of the second applicator as compared to the first applicator.

In embodiments, the first applicator can be a one-size fits all applicator. For example, the first applicator can be a conventional, two-dimensional face mask. For example, a cosmetic face mask such as SK-II Facial Treatment Mask (Procter and Gamble) can be used as the first applicator. In embodiments, the second applicator is an applicator that was created from a digital geometric representation of the target area. For example, the second applicator can be a custom-made three-dimensional face mask designed specifically for the user's face or a target portion thereof. Such custom-made three-dimensional face mask can be any of those described in U.S. Patent Application Publication Nos. 2017/008566, 2017/0354805, and 2017/0354806, the respective disclosures of which are incorporated herein by reference.

In any embodiments, the first applicator and the second applicator can both be two-dimensional structures, or both be three-dimensional structures, or the first applicator can be a two dimensional structure and the second applicator can be a three-dimensional structure. The methods in accordance with embodiments of the disclosure can illustrate the improvement in percent coverage or percent contact that can be achieved with the second applicator.

In embodiments, methods of the disclosure can be used in quality checks when manufacturing three-dimensional face mask. For example, in embodiments, the method can include receiving on a processor a first set of digital data representing at least a portion of the human face for which the mask was made, receiving on the processor a second set of digital data representing of the manufactured three-dimensional face mask or a corresponding portion thereof; digitally overlaying the second set of data over the first set of data; calculating at a plurality of points of the overlay a separation distance between the second set of data and the first set of data. The second set of data, for example, can be received from a digital geometric representation of the three-dimensional face mask. A separation distance of about 1 mm or less can be used as a threshold for contact between the face and the three-dimensional face mask. In embodiments, a separation distance of 1 mm or less at least 90% of the plurality of points can represent a properly manufactured three-dimensional face mask.

Throughout the discussion below reference will be made to the second set of data. It should be understood herein that similar steps, adjustments, manipulations, and uses of the data disclosed herein with reference to the second set of data can be applicable to the third set of data or any set of data similarly associated with an applicator.

In any of the embodiments therein, the digital geometric representation of the target area, an applicator, and/or the manufactured three-dimensional mask can be streamed in real time, received from a memory, or received direct from the capture source, such as a three-dimensional scanner. In any of the embodiments, the digital geometric representation of the target area or the application can be obtained using one or more of three-dimensional scanners, two-dimensional scanners, cameras, smartphone camera, digital applications for tablets and phones, and other known equipment for obtaining digital geometric data. An Artec Spider, available from Artec Group Palo Alto, Calif. is an example of a suitable three-dimensional scanner. An example mobile application for a cellular phone or table is 123D Catch from Autodesk or Bellus3D from Bellus3D.

The digital geometric representation of the target area or the applicator can be used as a whole or partitioned with only a portion of the total representation being used. Furthermore, portions of the geometry derived from the scan or other imaging technique can be removed or edited from the digital geometric representation. The digital geometric representation data may be used without alteration, or the geometry of the representation may be altered. For example, digital processing (e.g. smoothing, gap filling, interpolation, down sampling, etc.) may be used to alter the digital data. For example, the digital data can be altered to be provided as a mesh to allow for measurement of various features on the digital data. For example, a two-dimensional set of data from an image or scan can be altered to provide a three-dimension representation of the two-dimensional data.

In any of the embodiments of the disclosure, any one or more of the various digital processing equipment, digital geometric representations, graphics programs, and graphical displays may be stored in a tangible computer readable memory or medium and/or shared or cloud-based medium, and execute one or more processors to perform the functions described herein. For example, in embodiments, the digital geometric representation can be obtained by a user using a smartphone camera and/or mobile application and subsequently uploaded to a manufacturer's shared memory or medium for manufacturing of the mask. In other embodiments, digital geometric representations can be obtained with scanners or other imaging devices located at the point of sale of the mask. The data from the digital geometric representations can be stored locally or on a shared medium.

In any of the embodiments disclosed herein, the digital geometric representation of the target area or the applicator can be stored on a memory or shared medium and transmitted to a processor. In any of the embodiments disclosed herein, the digital geometric representation of the target area or the applicator can be stored on a memory of the scanning or capture device and transmitted by the device or other means to a processor. For example, the scanning or capture device can store the digital geometric representation in whole or in part, including, on a buffer memory for transmitting the digital geometric representation to the processor in buffering mode.

In any of the embodiments disclosed herein, the target area can be a human face or portion thereof and the applicator can be a mask for covering the face or portion thereof. The mask can include or have applied thereto one or more cosmetic, therapeutic, and active agents for treating the face or skin or skin conditions thereon. The mask can be a two-dimensional mask (e.g. sheet mask, substrate, nonwoven, woven, knit, gel, film, foil or hydrogel mask or any other material) or a three-dimensional mask made of any material. In any of the embodiments disclosed herein, the three-dimensional mask can be a self-supporting mask. As used herein, the term "self-supporting" means that an element of or the applicator in its entirety retains a substantial portion of a defined three-dimensional shape without the aid of external support structures when resting on a horizontal surface in air. In any of the embodiments disclosed herein, the mask can be a single-dose applicator or for single use having a single-dose of the active, cosmetic, and/or therapeutic. As used herein, the term single-dose means an applicator comprising sufficient active agents to afford a user only a single application of the active agent via the applicator. In any of the embodiments disclosed herein, the mask can be for multiple use. For example, active, cosmetic, and/or therapeutic agents can be applied and successively reapplied for multi-use. In any of the embodiments disclosed herein, the mask can be disposable. As used herein, the term disposable refers to applicators intended to be discarded after use rather than durable, or semi-durable implements intended for multiple users either with or without the reapplication of an active agent. In any embodiment, the mask can be a durable item suitable for washing by hand or in a dishwasher or clothing washing machine.

In embodiments, the target area is a human face. The digital representation of the human face can be constrained in space from the backside to represent the bone internal to the skull. For example, in embodiments, the inner surface of the digital representation, corresponding to the underlying bone is treated as a rigid surface and constrained in space. The nodes on the inner surface of the skin are thus fixed in place and not allowed to move. This can be accomplished in known finite element simulation packages, for example, as a boundary condition.

In embodiments, the digital representation can be further modified to have mechanical properties simulating that of the target area. For example, when the target area is a human face the digital representation or resulting mesh can be given a thickness representing the skin surface. For example, the thickness can be about 0.5 mm to about 4 mm, about 1 mm to about 3 mm, or about 2 mm to about 4 mm. Other suitable thickness can be about 0.5, 1, 2, 3, or 4, mm. In embodiments, the thickness can be constant. In embodiments, the thickness can vary according to different regions of the target area or entire face. The digital representation or set of data resulting from the digital representation can be given material surface properties as, well. For example, where the target area is the human face, the digital representation or digital data can be given properties to simulate the mechanical properties of the dermis and epidermis layers. For example, a stiffness model can be used to simulate the mechanical properties for the epidermis and dermis as a single bulk layer. The model can include specification of one or more properties including for example, the stiffness, Poisson ratio, and viscoelastic behaviors. Alternately, the mechanical properties of the dermis and epidermis layers can be simulated as two separate layers.

In embodiments, the second set of data represents the applicator. The second set of data can be manipulated, for example, from a digital representation to a mesh. In embodiments, the second set of data can be further manipulated to include mechanical properties of the material of the applicator. For example, in embodiments, the applicator can be rigid and such rigidity can be simulated in the second set of data. In other embodiments, the applicator can be flexible. In embodiments in which the second or third set of data represents a two-dimensional mask, mechanical properties of a wet cotton substrate SKII FTE mask can be used, for example.

In yet other embodiments, the applicator can be a self-supporting structure and such resilient nature of the applicator under applied force can be similarly simulated in the second set of data. In embodiments, the applicator can have an active, therapeutic, cosmetic or other agent applied thereto. The adhesive nature of such ingredients on a mask can be incorporated into the second set of data to simulate the self-adherent property of an applicator on a target surface. In embodiments, the second set of data can be manipulated to simulate a wet applicator or a dry applicator.

In accordance with embodiments, the mask or applicator can include any suitable active, cosmetic, or therapeutic agent to be applied to the face of the user. For example, active, therapeutic, and/or cosmetic agents can include active ingredients, carriers, chassis, emulsions, hydrogels, adhesives, process aides (such as thickeners, rheology modifiers, etc.). Active agents may further comprise a release layer to help active agents transfer from the applicator to the target surface. Active agents may include adhesive materials, active chemical agents, absorbent materials such as absorbent gel materials or absorbent foam materials placed according to either the diagnostic scan or relative to identifiable features. As an example, it may be desirable to dispose an absorbent foam material along cheekbones, brow or nose of a scanned user's facial mask, the disposition sites may be determined according to the geometry of the representation rather than according to the diagnostic scan of the user. Active agents may be in one or more physical forms, including but not limited to: foams, liquids, powders, films, fibers, creams, gels, hydrogels, encapsulated active agents, solids, combinations of these forms and other forms. Some examples of active agents include but are not limited to: moisturizer, anti-aging, anti-wrinkle, skin tone control, anti-irritation, sensates (e.g. menthol), heating or cooling chemistries, skin tightening, hair removal, hair regrowth, fungicide, antibacterial, antiviral, surfactants, cleaning agents, copper ion eluting (such as from Cupron of Richmond, Va.), antioxidants, vitamins, sunscreen, rejuvenation agents, wound healing agents, sebum management agents, astringents, exfoliates, anti-inflammatory, leave on, overnight, dry skin, itchy skin, cracked skin, peptides, acne, scar treatments, sore muscles treatments, medicaments including pharmacological actives to treat disease states or other acute or chronic issues such as eczema, rashes, acne, cancer, cold sore, Psoriasis, Rosacea, Vitiligo, warts, Herpes, fungal infection, Actinic Keratosis, ulcers, shingles, poison ivy, and insect bites. Further, the medicaments, including pharmacological actives, can go beyond topical effect and be designed for transdermal delivery of an active into the bloodstream or other internal tissue. Examples of therapies, both prescribed and un-prescribed include: nicotine, Botox, and hormone supplements.

Exemplary active agents for cosmetic changes to the target structure include: hydrating agents, acne treating agent, anti-aging agents, ant-wrinkle agents, matte-finish compounds, under-eye hydrating agents, anti-oil agents, primer, lipstick, lip gloss, lip liner, lip plumper, lip balm, lip conditioner, lip primer, lip boosters, concealer, foundation, powder, rouge, blush, blusher, contour powder/creams, highlight, bronzer, mascara, eyeliner, and setting materials, scents, perfume or fragrance compositions (e.g. essential oils).

In one embodiment, the inclusion of one or more scents, perfume or fragrance compositions may be applied to the mask for subsequent deposition to the face. However, a portion, or all, of the included one or more scents, perfume or fragrance compositions may act as experience agents. The experience agent provides a smell in the environs of the mask when in use. For example, the smell provided by a fragrance to suggest outdoor flower garden aroma may be desirable when applying cosmetic agents to the face of a consumer/wearer. Experiential agents need not necessarily be located on the target structure contact surface of the mask. The agents may be located in a region not in contact with the target structure, such as on a non-contacting portion of the application side of the applicator or anywhere on any applicator side that is non-contacting to the target structure. The experience agent may be selected to accompany a selected appearance feature. In one embodiment, the indicia may comprise the active agent deposited upon the first structural element without alterations to the relative color or texture of the application site.

In embodiments, any of the foregoing properties or materials can be simulated in the second set of data where such materials or ingredients may affect the mechanical properties of the applicator, the positioning and/or retention of the applicator on the target surface.

In embodiments, the calculation of separation distance between an applicator and a target area can include converting the first set of data to a first mesh and converting the second set of data corresponding to the applicator to a second mesh and aligning the two meshes using software such as, but not limited to, Artec Studio 12 Professional (Artec Software). Any of the disclosure herein is similarly applicable to the overlying of the third and first sets of data or any other set of data associated with an applicator and target area. The meshes can be imported into the software in any suitable file format, including, for example, STL, OBJ, PLY, and other 3D mesh file formats. Once imported, the first mesh and the second mesh are manually brought into rough alignment. The first mesh, corresponding to the target surface, can be designated as fixed or registered and the second mesh can be designated as unregistered, thereby allowing the second mesh to be moved relative to the first mesh. Once roughly aligned, an align feature of the software can be used to bring the first and second meshes into refined alignment. Once aligned, both meshes can be selected and a measurement feature of the software can be used to calculate a distance between the two meshes at one or more points.

For example, a surface-distance map calculation can be used. In embodiments, the search distance can be selected to be up to 10 mm, which represents the maximum distance between points in space the program will search for calculating separation distance. If a gap is greater than the search distance, that gap will not be included in the calculation. Any suitable search distance can be used. Once calculated, an electronic image illustrating the calculated distances graphically can be displayed.

In other embodiments, the first and second set of data can be overlaid to simulate application of the applicator to the target surface. Any of the disclosure herein is similarly applicable to the overlying of the third and first sets of data. For example, the second set of data corresponding to the applicator can be positioned a distance from the first set of data and a digitally applied force can be used to push the second set of data against the first set of data, thereby simulating application of the applicator to the target area. For example, the applied force can be a distributed force on the applicator or can be a localized force on the applicator. For example, in embodiments an initial load can be provided as localized points of force, can be applied to push the second set of data to the first set of data, simulating application of the applicator and positioning of the user's fingers on the applicator applying the localized load to position the applicator onto the target area. Optionally, a distributed force can be applied to the second set of data after it is pushed against the first set of data, simulating a user applying further force across the applicator to better adhere or smooth the applicator to the target area. The adhesive force can also be used or incorporated into the force simulation for application and retention of applicator on the target surface. For example, wet applicators can include agents such as lotions, therapeutic agents, and other cosmetic agents that provide adhesive force. Additionally, or alternatively, wet applicators can include a water component or have water added thereto to make the applicator adhere to the target area. In embodiments, adhesive force of an applicator can be assessed using a peel test, in which the force required to peel the wet applicator away from the target area is measured, and provides the resulting adhesive force per unit area. Such force can be incorporated into the set of data representing the applicator to incorporate the adhesive force as an element to the simulation of the applicator being applied to and retained on the target area. Any suitable applications of force and associated loads can be used and will vary depending on the target area and type of applicator being applied to the target area. Suitable force profiles and loads can be readily determined by the skilled person based on typical application of the applicator or measured by actual application of an applicator.

In embodiments, the applicator can be a two-dimensional applicator. In such embodiments, a finite element analysis can be used to bring the flat applicator surface into contact with a three-dimensional target area before application of the load.

In embodiments, the method can include a further step of removing the load after the second set of data is pushed into contact with the first set of data. The load can be removed for example, when a force balance is detected and steady state of force is achieved. The overlaid data can be manipulated in embodiments to include a representation of the cohesive force of the applicator resulting, for example, from the ingredients applied to the inner surface of the applicator.

In embodiments, a static load or dynamic load can be used. Application of a dynamic load can be applied to allow the data sets to move relative to each other. In embodiments, steady state can be detected by a balance of force, and representing the point at which the objects stop moving relative to each other. The load can then be removed. In embodiments, the data sets representing the applicator and the target area can again be allowed to move relative to each other until motion ceases. For example, this can simulate any compression of the skin layer and then subsequent relaxation and motion after force is removed.

In embodiments, once the overlaid model reaches a converged solution, any gaps or bubbles or other separations between the first and second sets of data can be measured at one or more points. Any known software or algorithm for measuring the distance between two points can be used. For examples, a next nearest neighbor algorithm can be used to find the distance between a point in the set of the second data and its next nearest neighbor in the first set of data. In embodiments, the separation distance can be measured through a digital subtraction of pixels between a digital geometric representation of the first set of data and an overlaid digital geometric representation of the second set of data. In embodiments, the separation distance can be calculated using the mask and face geometries as the bounds of a solid structure and effectively digitally cast a part using the two surface as outer bounds. The thickness of the digitally cast part can then be measured to determine the spacing between the first and second sets of data. This may be reported, for example, as a difference volume between the two surfaces.

In embodiments, the separation between the sets of data can be measured at a plurality of points in a given target area. For example, where the applicator is a mask for a human face, the separation distance can be measured at one or more areas. For example, the separation can be measured in one or more of the under-eye region, the nose region, around the mouth, at one or both cheeks, for instances near the cheek bones, and around the jaw line. Any other regions of a given structure or a distribution of measurements across the applicator can also be used. As noted, above, a separation distance of 1 mm of less at any point can be indicative of contact between the applicator and the target area. A separation distance of 1 mm or more can be indicative of a gap or separation between the applicator and the target area. In embodiments, different separation distances may be used as the threshold depending on the target area and type of applicator. For example, separation distances can be about 2 mm, 3 mm, 1 mm, 0.5 mm or any values in between. Alternately, a continuum of separation distances from 0 mm to 10 mm may be visualized to show portions in good contact and portions in poor contact.

To assess the effectiveness of contact (the fit) provided by a mask several metrics can be used, such as, but not limited to mean error Root mean square error, mean absolute deviation, and mean of signed distances. In embodiments, a histogram of error can be used or a portion of the histogram such as the 90th percentiles, 95th percentile, or any other percentile. In embodiments, absolute error in a specific region can be used. For example, error in the high curvature regions like the eye sockets, edge of nose, brow, and chin can be used as metrics to assess the fit. Alternately, other regions that may impact fit can be assessed, such as the edge of cheeks near ears or the jaw line. Different regions of the target area can have different sensitivity to amount of error in terms of fit perception, and assessment of the fit can be tailored accordingly.

In embodiments, in a given target area having at least 90% of the plurality of points measured in that area with a separation distance of 1 mm or less is indicative of the applicator providing effective contact with that target area. In embodiments in which the method is used as a manufacturing quality check, having at least 90% of the plurality of points measured in a given target area with a separation distance of 1 mm or less is indicative of the applicator being properly manufactured. In any embodiments, a percentage in a given target area of a separation distance of 1 mm or less of about 90% to about 100%, about 95% to about 100%, about 92% to about 100, or about 96% to about 100% can be indicative of effective contact and/or proper manufacturing of the applicator. Other suitable percentages include about 90, 91, 92, 93, 94, 95, 96, 97, 98, 99, 99.9 and 100%.

Example

A visualization of a fit of a mask was obtained by first obtaining a first set of data of the user's face using a three-dimensional scan of the user's face and receiving that data on a process. A second set of data associated with the build of a three-dimensional mask was then received on the processor.

The first set of data associated with the user's face was provided a virtual model and assigned a thickness of approximately 2 mm. The backside or internal face of the virtual model of the human face was constrained in space to represent the bone internal to the user's skull. The 3 mm thick surface layer was meshed and digitally given mechanical properties to simulate the combined dermis and epidermis layers of the skin.

The second set of data was meshed and given properties to match the mechanical properties of the material from which the mask is formed.

The outer surface of the mask was digitally pushed toward the virtual model of the face through application of a distributed force to represent the loading equivalent of typical application of the mask by a user. Once the model reached a solution in which the forces were balanced, the load was removed and a cohesive force was applied between the mask and the virtual model of the face, representing the adhesive force created by the active, therapeutic, and/or cosmetic agent(s) provided on the mask. As the model reached a force balance again, representing a converged solution, the remaining gaps between the face and the mask were measured. A difference map illustrating the separation distance between the face and the mask at various regions as then generated, as is illustrated in FIG. 7.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for evaluating a fit of an applicator on a target area, comprising:
   receiving on a processor a first set of digital data representing the target area, the first set of digital data being received from a digital geometric representation of the target area stored on a memory or streamed in real time;
   receiving on the processor a second set of digital data representing at least a portion of an applicator designed to contact the target area;
   digitally overlying the second set of digital data over the first set of digital data to determine digitally the contact area of the at least the portion of the applicator when applied to the target area;
   calculating in the target area at a plurality of points of the overlay a separation distance between the second set of digital data and the first set of digital data, wherein a separation distance of about 1 mm or less represents contact between the applicator and the target area when the applicator is applied to the target area;
   determining a percentage of the plurality of points having a separation distance of about 1 mm or less in the target area, wherein a determination of at least 90% of the plurality of points having a separation distance of 1 mm or less indicates the applicator fits; and
   generating a first electronic image that includes a visual depiction of the calculated separation distance between the applicator and the target area when the applicator is applied to the target area, wherein the first electronic image includes a continuum of separation distances at a plurality of points.

2. The method of claim 1, wherein the second set of digital data is received from a digital geometric representation of the at least a portion of the applicator.

3. A method for comparing a fit of a first applicator to a second applicator when applied to a target area, comprising:
   receiving on a processor a first set of digital data representing the target area, the first set of digital data being received from a digital geometric representation of the target area stored on a memory;
   receiving on the processor a second set of digital data representing at least a portion of a first applicator designed to contact the target area, wherein the first applicator is a one-size fits all applicator;
   receiving on the process a third set of digital data representing at least a portion of a second applicator designed to contact the target area, wherein the second applicator is created from a digital geometric representation of the target area;
   digitally overlying the second set of digital data over the first set of digital data to determine digitally the contact area of the at least the portion of the first applicator when applied to the target area;
   digitally overlying the third set of digital data over the first set of digital data to determine digitally the contact area of the at least the portion of the second applicator when applied to the target area;
   calculating in the target area at a plurality of points of the overlay a separation distance between the second set of digital data and the first set of digital data, wherein a separation distance of about 1 mm or less represents contact between the first applicator and the target area when the first applicator is applied to the target area;
   calculating in the target area at a plurality of points of the overlay a separation distance between the third set of digital data and the first set of digital data, wherein a separation distance of about 1 mm or less represents contact between the second applicator and the target area when the second applicator is applied to the target area;
   determining a percentage of the plurality of points having a separation distance of about 1 mm or less in the target area, wherein a determination of at least 90% of the plurality of points having a separation distance of 1 mm or less indicates the applicator fits;
   generating a first electronic image that includes a visual depiction of the calculated separation distance between the first applicator and the target area when the applicator is applied to the target area; and
   generating a second electronic image that includes a visual depiction of the calculated separation distance between the second applicator and the target area when the applicator is applied to the target area,
   wherein the first and second electronic images includes a continuum of separation distances at a plurality of points.

4. The method of claim of claim 3, comprising determining a percentage of the plurality of points having a separation distance of about 1 mm or less the target area for the first and second applicators and generating a third electronic image that includes a visual depiction of regions in which at least 90% of the plurality of points have a separation distance of 1 mm or less only in the overlay of the third set of digital data with the first set of digital data and not in the overlay of the second set of digital data with the first set of digital data, thereby visually depicting improved coverage of the second applicator as compared to the first applicator.

5. The method of claim 3, comprising displaying the first and second electronic images side-by-side.

6. The method of claim 3, comprising displaying the first electronic image before displaying the second electronic image.

7. The method of claim 3, wherein the second electronic image comprises color mapping to visually depict the calculated separation distances.

8. The method of claim 3, wherein the first electronic image comprises color mapping to visually depict the calculated separation distances.

9. The method of claim 3, wherein the applicator is a face mask and the target area is at least a portion of a human face, the applicator contacting skin on the at least a portion of the human face.

10. The method of claim 9, comprising manipulating the first set of digital data to simulate a thickness and/or mechanical properties of the skin.

11. The method of claim 9, comprising, during digital overlaying of the second set of digital data and/or the third set of digital data, constraining the first set of digital data in a region corresponding to the backside of the human face to simulate bone structure of the human face.

12. The method of claim 3, comprising manipulating the second set of digital data to simulate mechanical properties of the applicator.

13. The method of claim 12, comprising manipulating the second set of digital data to simulate a rigid applicator.

14. The method of claim 12, comprising manipulating the second set of digital data to simulate a flexible applicator.

15. The method of claim 12, comprising manipulating the second set of digital data to simulate a wet applicator.

16. The method of claim 12, comprising manipulating the second set of digital data to simulate a dry applicator.

17. The method of claim 3, comprising manipulating the third set of digital data to simulate mechanical properties of the applicator.

18. The method of claim 17, comprising manipulating the third set of digital data to simulate a rigid applicator.

19. The method of claim 17, comprising manipulating the third set of digital data to simulate a flexible applicator.

20. The method of claim 17, comprising manipulating the third set of digital data to simulate a wet applicator.

21. The method of claim 17, comprising manipulating the third set of digital data to simulate a dry applicator.

22. The method of claim 3, wherein the first applicator is a flat, two-dimensional applicator and the second applicator is a three-dimensional application.

23. The method of claim 3, comprising comparing the percentage of points in the first electronic image having a separation distance greater than 1 mm to a percentage of points in the second electronic image having a separation distance greater than 1 mm.

24. The method of claim 3, wherein the target area comprises an under-eye region of the human face.

25. The method of claim 3, wherein the target area comprises a nose of the human face.

26. The method of claim 3, wherein the first set of digital data is received from a digital representation of the target area stored in full on a memory.

27. The method of claim 3, wherein the first set of digital data is received from a memory or buffer memory of an image capture device.

28. The method of claim 3, wherein the first set of digital data is stored on a memory associated with mobile application and transmitted to the processor by the mobile application.

29. The method of claim 3, wherein the second set of digital data is received from a digital geometric representation of the first applicator stored on a memory.

30. The method of claim 3, wherein the third set of digital data is received from a digital geometric representation of the second applicator stored on a memory.

* * * * *